(12) United States Patent
Quirynen et al.

(10) Patent No.: US 11,950,001 B2
(45) Date of Patent: Apr. 2, 2024

(54) AUTOMATED CALIBRATION OF HEAD-MOUNTED HANDS-FREE CAMERA

(71) Applicant: Rods & Cones Holding bv, Amsterdam-Duivendrecht (NL)

(72) Inventors: Benoit Quirynen, Amsterdam-Duivendrecht (NL); Jan Dheedene, Amsterdam-Duivendrecht (NL); Bruno Dheedene, Amsterdam-Duivendrecht (NL); Dario Vuljanic, Amsterdam-Duivendrecht (NL); Dalibor Kofjac, Amsterdam-Duivendrecht (NL)

(73) Assignee: Rods & ConesHolding bv, Amsterdam-Duivendrecht (NL)

( * ) Notice: Subject to any disclaimer, the term of this patent is extended or adjusted under 35 U.S.C. 154(b) by 0 days.

(21) Appl. No.: 17/875,393

(22) Filed: Jul. 27, 2022

(65) Prior Publication Data
US 2023/0067410 A1    Mar. 2, 2023

(30) Foreign Application Priority Data

Aug. 25, 2021 (BE) .................................. 2021/5674
Jul. 15, 2022 (EP) .................................. 22185303

(51) Int. Cl.
| | |
|---|---|
| *H04N 23/959* | (2023.01) |
| *G02B 27/01* | (2006.01) |
| *H04N 5/77* | (2006.01) |
| *H04N 13/332* | (2018.01) |
| *H04N 17/00* | (2006.01) |
| *H04N 23/67* | (2023.01) |
| *H04N 23/68* | (2023.01) |

(52) U.S. Cl.
CPC ............. *H04N 23/959* (2023.01); *H04N 5/77* (2013.01); *H04N 13/332* (2018.05)

(58) Field of Classification Search
None
See application file for complete search history.

(56) References Cited

U.S. PATENT DOCUMENTS

| | | | |
|---|---|---|---|
| 4,621,283 A | 11/1986 | Feinbloom | |
| 2012/0249424 A1* | 10/2012 | Bove ..................... | A63F 13/211 345/158 |
| 2015/0193983 A1* | 7/2015 | Katz ........................ | G06F 1/00 345/419 |
| 2017/0161956 A1* | 6/2017 | Fu ........................... | G06F 3/012 |
| 2020/0404159 A1 | 12/2020 | Lei et al. | |
| 2021/0027496 A1* | 1/2021 | Koyama ................... | G06T 7/73 |
| 2021/0173275 A1 | 6/2021 | Osterhout | |
| 2022/0039904 A1* | 2/2022 | Govari .................... | A61B 90/37 |

FOREIGN PATENT DOCUMENTS

EP    3278756 A1    2/2018

\* cited by examiner

*Primary Examiner* — Hung Q Dang
(74) *Attorney, Agent, or Firm* — Hodgson Russ LLP

(57) ABSTRACT

A head-mounted device can be automatically calibrated using an image sensor and at least one sensor system for detecting translation and rotation of the head-mounted device. Parameters under which the image sensor operates can be automatically calibrated when a detected translation remains below a predetermined translational threshold and a detected rotation remains below a predetermined rotational threshold for at least a predetermined period of time. The head-mounted device can be used by a medical professional in a surgical procedure.

18 Claims, 3 Drawing Sheets

AUTOMATED CALIBRATION OF HEAD-MOUNTED HANDS-FREE CAMERA

CROSS-REFERENCE TO RELATED APPLICATIONS

This application claims priority to the European Patent App. No. 22185303.9 filed Jul. 15, 2022, which claims priority to Belgian Patent App. No. 2021/5674 filed Aug. 25, 2021, the disclosures of which are hereby incorporated by reference.

TECHNICAL FIELD

The invention relates to head-mounted devices with an image sensor or camera, such as smartglasses, headsets with a camera, but also headgear on which a (detachable or not) camera or camera module is provided. Specifically, the invention further relates to the automatic focusing of this camera, and the calibration of the operational parameters of the camera, such as focus length, shutter speed, lens distortion, camera angle, etc., and seeks an automated and hands-free way of performing a calibration, such as during use in a surgical operation, but also in other processes where a user should not or cannot use their hands to calibrate the image sensor.

PRIOR ART

In the prior art, head-mounted image sensor devices, such as, for example, smartglasses, are increasingly being used to perform sensitive operations, sometimes with external guidance. These systems have one or more image sensors (cameras), which have become more sophisticated over the years and have gained many functionalities. Thus, these image sensors can operate under a very wide range of operational parameters, such as focus distance, shutter speed, resolution (image quality), color balance, lighting support, etc.

Such devices often also have their own screen. For example, the user can sometimes zoom in or zoom out on certain things, save certain images (in a certain perspective), and other operations, and then reuse these images later, during another part of the operation. In addition, external supervisors can also use these images for follow-up, or for specific guidance, for example by giving comments, or visually indicating and displaying the edited images to the user.

In these very diverse applications, it is therefore necessary to have a flexible image sensor, which can easily, quickly, and accurately capture images in different configurations (exposure, focal length, resolution, etc.). Due to the additional difficulty that in some situations it is impossible to use the hands for this, or very disadvantageous (endangering sterility during an operation), other solutions must be sought. For example, it is possible to work via voice control, but this is often subject to other problems (again with the example of a medical procedure, mouth masks are often used, which can distort or weaken the voice and the system may not recognize it). Moreover, in such cases it is also necessary to know all the correct "signals" beforehand, as each system typically has a different trigger to perform certain actions.

The present invention aims to find a solution for at least some of the above problems.

SUMMARY OF THE INVENTION

The invention relates to an improved head-mounted device having a sensor system for detecting translation and rotation of the head-mounted device, an image sensor for capturing images.

The device is configured to automatically calibrate certain operating parameters of the image sensor under certain conditions. These conditions amount to the wearer holding their head still (and thus the device itself) for a certain length of time.

In particular, the invention relates to a head-mounted device according to the embodiments disclosed herein.

In a second aspect, the invention relates to a use of a head-mounted device according to the first aspect in a medical procedure, by a medical professional.

Additional possible uses are repair work in hard-to-reach locations (work at height, remote places, etc.), wherein users do not have to fully master all aspects of their task, due to the possibility of remote assistance via the device based on the images it captures.

In a third aspect, the invention relates to a method of imaging with a head-mounted device according to the first aspect, wherein the calibration of the image sensor is performed under certain conditions.

DETAILED DESCRIPTION

Figure 1:
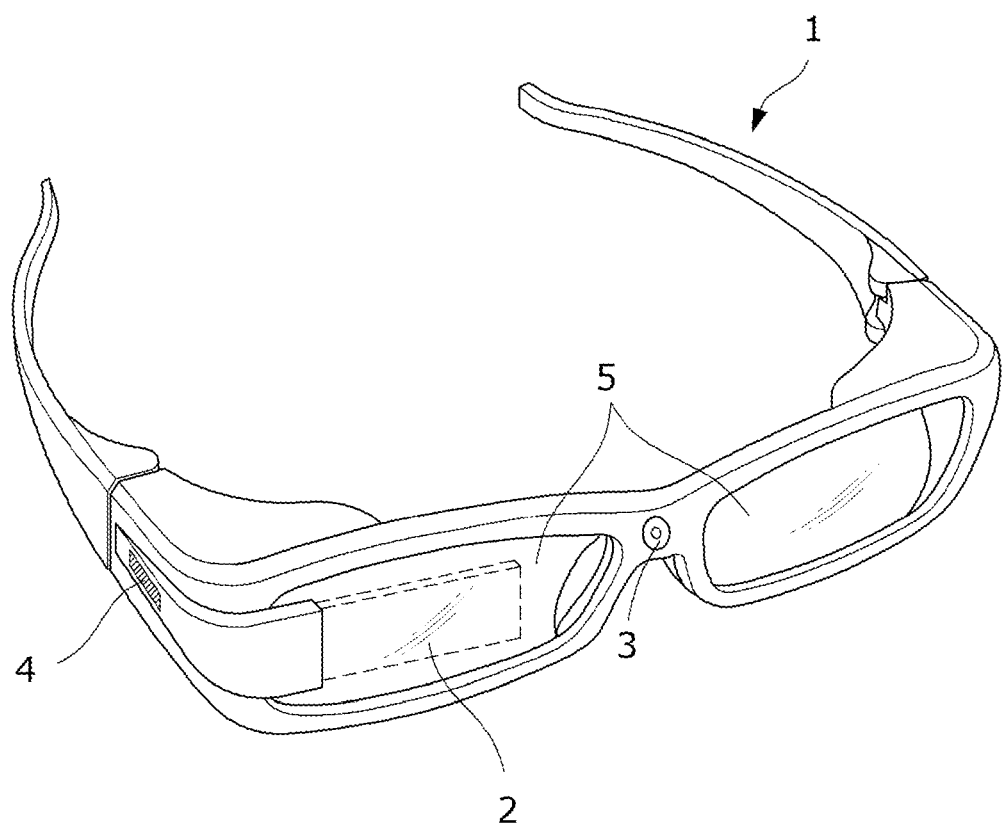
FIG. 1 shows an embodiment of a head-mounted device according to the invention in the form of smartglasses with a display, with all components provided on the head-mounted device.

Unless otherwise defined, all terms used in the description of the invention, including technical and scientific terms, have the meaning as commonly understood by a person skilled in the art to which the invention pertains. For a better understanding of the description of the invention, the following terms are explained explicitly.

In this document, "a" and "the" refer to both the singular and the plural, unless the context presupposes otherwise. For example, "a segment" means one or more segments.

When the term "around" or "about" is used in this document with a measurable quantity, a parameter, a duration or moment, and the like, then variations are meant of approx. 20% or less, preferably approx. 10% or less, more preferably approx. 5% or less, even more preferably approx. 1% or less, and even more preferably approx. 0.1% or less than and of the quoted value, insofar as such variations are applicable in the described invention. However, it must be understood that the value of a quantity used where the term "about" or "around" is used, is itself specifically disclosed.

The terms "comprise', "comprising', "consist of", "consisting of', "provided with', "have', "having', "include', "including', "contain', "containing" are synonyms and are inclusive or open terms that indicate the presence of what follows, and which do not exclude or prevent the presence of other components, characteristics, elements, members, steps, as known from or disclosed in the prior art.

The term "image sensor" refers to any electrical or electronic component capable of capturing information that can be used for imaging, such as CCD or CMOS sensors, and typically refers to a camera (digital or analog).

Quoting numerical intervals by endpoints comprises all integers, fractions and/or real numbers between the endpoints, these endpoints included.

In a first aspect, the invention relates to an improved head-mounted device having a sensor system for detecting translation and rotation of the head-mounted device and an image sensor for capturing images.

The device is configured to automatically calibrate certain operating parameters of the image sensor under certain conditions. These conditions amount to the wearer holding their head still (and thus the device itself) for a certain length of time.

Head-mounted imaging devices, such as smartglasses and related devices, are increasingly being used for operations where remote assistance or monitoring is used to support the user(s) on site. The remote aspect can be due to limited space, great distance, difficult accessibility, or other physical impediments (such as sterility requirement during medical procedures, physical limitations of a person monitoring remotely), but can also be practical and has the further advantages that it saves a lot of time and costs (including in terms of transport and preparation).

This remote assistance and monitoring relies on image quality. This is because the remote users rely on the images recorded locally by the mobile head-mounted device, and which are made available to the remote users. In many of these operations, the sharpness and clarity of the images is a crucial part. For example, it could involve medical procedures, where a team of doctors remotely oversee and guide certain parts of a procedure, and for this need very accurate images, given the scale on which surgery is often performed, for example for a craniotomy. Industrial applications can also be taken into account, such as technical maintenance/installation/etc. of certain devices. In each of these cases, it is important that the remote users get a clear view of the scene. Whereas for the on-site user this is of course taken care of by the eye, this is not the case for the image sensor with which remote users receive images. Because, as mentioned above, it is not always possible, a matter of course, or recommended that the on-site user manually initiate this adjustment or calibration, other mechanisms are sought, namely, holding the head-mounted device still, which indicates holding the user's head still on-site, and this is used as a trigger for calibrating the image sensor.

Holding the head-mounted device still is detected by the sensor system in the device, wherein holding still is considered to be the translation of the device over a length of time remaining below a predetermined translational threshold, preferably 5.0 cm or more preferably 2.0 cm. Account is taken here of an absolute translation over that time, i.e. a position difference that preferably amounts to a maximum of 5.0 or more preferably 2.0 cm between the two most extreme positions of the device in that time. Note that in some cases, this translational threshold can be set higher, such as for example 5.0 cm, 4.0 cm, 3.0 cm, or even higher values. Preferably, however, it is set lower, such as 1.0 cm, 0.5 cm, 0.25 cm or lower. Furthermore, a user can also set that the condition to remain below the translational threshold does not apply, for example in environments where translation cannot be avoided (e.g. when working on a tower crane, which is subject to another object's movement). In still other versions, the translation relative to an external object (other electronic device wired or wirelessly connected to the device) can be used, which must then remain below a translational threshold.

In a second condition, holding still is considered to be the rotation of the device over the predetermined time, which remains below a predetermined rotational threshold of 10.0°, preferably 5.0°. Again, the detected rotation over a given time here refers to the difference in rotation between the two most extremal positions in the given time (e.g. a first extremal position is rotated X° relative to starting position about a given axis, the second is rotated Y° in the other sense about the particular axis, results in a total rotation over that length of time of X°+Y°). Again, this can be adjusted according to the application (as indicated, in situations with external movements) to higher values, such as 12.5°, 15.0°, 17.5° or even 20.0°. Alternatively, it is also possible to work again with a relative rotation with respect to an external element (electronic device, such as a smartphone or a dedicated device for this purpose). In this way, external movements, such as with a moving surface, are also compensated.

It should be understood that the invention can be extended to the application of only one of the two conditions. This can be useful, for example, in situations where unwanted movements or rotations are difficult or impossible to prevent/predict (as mentioned, on a tower crane or high building).

In a preferred embodiment, the predetermined length of time is at least 0.5 s, more preferably at least 1.0 s, even more preferably at least 2.0 s or at most 2.0 s, at least 4.0 s, or even 5.0 s.

In a preferred embodiment, the predetermined translational threshold is at most 5.0 cm, preferably at most 2.5 cm, and more preferably at most 1.0 cm.

In a preferred embodiment, the predetermined rotational threshold is at most 10.0°, and preferably at most 5.0°.

In a preferred embodiment, the predetermined length of time is at least 1.0 s, and preferably at least 2.0 s. The predetermined translational threshold is at most 5.0 cm, preferably at most 3.0 cm, preferably at most 2.5 cm, and more preferably at most 1.0 cm. The predetermined rotational threshold is at most 10.0°, and preferably at most 5.0°.

Alternatively, conditions on acceleration (translational or rotational) can be imposed, wherein holding the device still for a specified time means that no translational acceleration takes place above a predetermined translational acceleration threshold and/or no angular acceleration takes place above a predetermined angular acceleration threshold. The translational velocity threshold here is preferably about 10.0 cm/s$^2$, more preferably about 5.0 cm/s$^2$, even more preferably 2.5 cm/s$^2$, and even more preferably 1.0 cm/s$^2$. The rotational velocity threshold here is preferably approximately 10.0°/s$^2$, more preferably about 5.0°/s$^2$, even more preferably 2.5°/s$^2$, and even more preferably 1.0°/s$^2$.

By using an external component, the relative movement or acceleration of the head can often be better detected, as general movements of the body are compensated. For example, while driving in a car, a movement or acceleration of the head can take place, but this is only the result of the total displacement of the body. By taking into account an external component, which is worn by the user, this contribution can be compensated in order to determine the effective movement. The determination of the movement/acceleration with respect to the external component can be done in several ways, for example by also detecting the movement/acceleration on the external component and determining the difference, or by working with a beacon, allowing to directly determine the movement/acceleration of the head-mounted device relative to the beacon.

In one embodiment of the head-mounted device, alternatively or additionally, the velocity (translational and/or rotational) may be used to determine whether the head-mounted device is being held still (and subsequent calibration must take place), following the same principles as described above. This is checked by seeing if the translational and/or rotational velocity remains below a predetermined translational and/or rotational velocity threshold. The translational velocity threshold here is preferably about 5.0 cm/s, more preferably about 2.5 cm/s, even more preferably 1.0 cm/s, and even more preferably 0.5 cm/s. The rotational velocity threshold here is preferably about 5.0°/s, more preferably about 2.5°/s, even more preferably 1.0°/s, and even more preferably 0.5°/s.

To this end, the sensor system can be equipped with a number of components suitable for detecting translational movements and/or rotational movements, but alternatively or additionally also for detecting translational and/or rotational velocities and/or accelerations. Typically, the sensor system will comprise one or more accelerometers and/or gyroscopes. In this sense, an accelerometer and gyroscope can be used to detect an acceleration, and from there calculate the movement/rotation.

The image sensor typically faces away from the user when worn, although in some cases it is movably mounted on the device. In some applications, such as for example smartglasses, several image sensors can be provided, wherein at least one of the image sensors can be calibrated as described in this document. In many situations, the recorded image from the image sensor substantially corresponds to what the user wearing the device on his or her head sees.

By configuring the device to automatically calibrate the parameters of the image sensor upon detection of the device "being held still" (basically keeping the head still), this allows the user to, without using their hands and intuitively, optimize the recorded images from the image sensor. Holding the head still for a length of time is a sign that the user (device wearer) finds the current position relevant, and that he or she is probably thoroughly reviewing the scene of the currently recorded images. For this reason, it is useful and advantageous to have the system automatically calibrate the parameters at such moments with which the images are recorded, and thus later formed. As a result, the user no longer has to actively intervene and endanger, for example, sterility, their concentration, or their safety.

To prevent the system from calibrating the parameter inappropriately, a minimum time is set for holding still before it is recognized as such and triggers a calibration. Again, this duration can also be adjusted according to the circumstances. Where time pressure is less relevant, or where calibration too often is undesirable, the duration can be set higher, for example 5.0 seconds or more, such as 6.0 s, 7.0 s, 8.0 s, 9.0 s, 10.0 s, 15.0 s or higher. If desired, it can also be set lower, such as after 0.5 s, 1.0 s or 1.5 s.

One of the main parameters that are calibrated is the focal length, which determines the distance at which the image sensor is focused. In an important application of this, namely the medical sector, it is important to be able to switch quickly and hands-free between different focal lengths for remote users, in order to give fast and correct feedback or instructions. Preferably, these instructions or feedback are also given through the head-mounted device, such as through a speaker built into it. Alternatively, a sound system can be provided externally at the location of the user wearing the device.

In a preferred embodiment, the calibration comprises automatically finding a shutter speed and/or a focal length appropriate for the circumstances, based on detection of incident light (ambient light) and distance from the part of the scene in focus.

In a preferred embodiment, the device is a pair of smartglasses. However, alternative embodiments may also be provided in the form of a helmet, headset or headband, or as modular components attached thereto.

In a preferred embodiment, the predetermined translational threshold is 0.5 cm, more preferably 0.25 cm, or 0.1 cm or even 0.05 cm. In a preferred embodiment, the predetermined rotational threshold is at most 2.5°, more preferably 1.0°, 0.5°, or even 0.25° or 0.1°. Preferably, both conditions are applied, both a translational threshold and a rotational threshold.

With the above threshold values, both in terms of movement, speed, and acceleration, an averaging or other processing is preferably performed by the device in order to filter natural vibrations and minimal movements, in order to avoid that the threshold would be exceeded by these small movements. For example, it is possible to average over a predetermined time to determine whether or not movement/speed and/or acceleration has actually been detected. Thus, under such vibrations and minimal unwanted movements, the device can detect that there is no threshold violation and proceed to calibrate the parameters of the image sensor.

In a preferred embodiment, the device is configured to perform the calibration if the detected translation is below the predetermined translational threshold and the detected rotation is below the predetermined rotational threshold for at least the predetermined length of time following the detection of a predetermined movement sequence of the head-mounted device, the detection being performed by the sensor system of the head-mounted device.

In a preferred embodiment, the device is configured not to perform a subsequent calibration until a translation and/or rotation of the head-mounted device that exceeds at least the predetermined translational threshold and/or the predetermined rotational threshold is detected by the sensor system.

In a preferred embodiment, the device is configured not to perform a subsequent calibration until the sensor system detects translation and/or rotation of the head-mounted device exceeding at least a predetermined movement threshold, the movement threshold at least two times higher than the predetermined translational threshold and rotational threshold.

The term "predetermined movement sequence" refers to a trigger for the system to verify whether or not movement (movement/acceleration/velocity) occurs within the predetermined length of time. This trigger can be a certain movement that the user performs "consciously" (for example, nodding, shaking, making a circular figure, or other patterns, more complex or not), but it can also simply be "a movement" that exceeds the predetermined threshold values (or preferably exceeds these thresholds at least by a factor of two or greater, such as 3, 4, 5 or greater, to ensure effective movement). This prevents the system from continuing to calibrate after a previous calibration when the head is held still for an extended length of time for no reason, such as a new movement/position/etc. A specific movement sequence offers the advantage that the user can simultaneously control this consciously and very simply and that unnecessary calibrations are avoided. By opting for "a movement" that exceeds the threshold values, calibration will take place more often, but no conscious action is required on the part of the user, who can thus also focus their full concentration on their task.

In a preferred embodiment, the sensor system comprises at least one gyroscope. A gyroscope can be used to measure the angular velocity and orientation of the head-mounted device and can thus be used to determine its change over time, to determine if the threshold values have been exceeded and whether or not the parameters of the image sensor have to be calibrated. In certain embodiments, two or three gyroscopes may be provided, wherein the gyroscopes are arranged to measure rotation relative to three mutually independent axes.

In a preferred embodiment, the sensor system comprises at least one accelerometer. An accelerometer is hereby used to measure the acceleration (and consequent speed and/or position) of the head-mounted device, and the change in the translational characteristics of the device over time, to determine if the threshold values have been exceeded and whether or not the parameters of the image sensor have to be calibrated.

In certain embodiments, two or three accelerometers may be provided, wherein the accelerometers are provided to measure the translational acceleration along three mutually independent axes.

In a preferred embodiment, the sensor system comprises at least one magnetometer, typically for determining a reference orientation of the system. In certain embodiments, two or three magnetometers may be provided, preferably at least one magnetometer along each of the three mutually independent axes.

In a preferred embodiment, the device comprises a display for displaying images, wherein a processor unit controls the display, and the display can be positioned to display the images visible to a user wearing the head-mounted device on their head.

The processor unit may be provided in the device itself, or on an external control unit that is wiredly or wirelessly connected to the head-mounted device and configured to control the device. An advantage of implementing the processor unit on the device is its compactness, and the possibility of omitting a wired connection (which can potentially be a nuisance) or omitting wireless communication components in the device, to make it as light as possible.

Providing the processor unit on an external control unit or pocket unit (for example a mobile phone, smartphone, dedicated device for this, etc.) has the advantage that the weight of the head-mounted device is reduced. This also allows to outsource other matters, such as power supply, to the external control unit, which also has a strong influence on the weight of the device.

Preferably, the connection between the external control unit and the head-mounted device is wired, as this allows energy supply along the same connection, as well as saves weight because no wireless communication components have to be provided (which is often also less energy efficient).

Preferably, the display is configured to display the images recorded by the image sensor. For example, these images can be further edited, annotated, or modified by the user or external parties (e.g. remote users). This allows, among other things, to enlarge or reduce the images, highlight certain elements or zones, add annotations (instructions, etc.) and other things, which can help the user in performing their tasks on site.

In the most preferred embodiment, the components with processing power (processors and the like) are all provided on the external control unit, so as to reduce as much as possible the weight of the head-mounted device, as well as the heat generation that occurs with major operations. In addition, if the power supply is also from the control unit, this ensures that only a reduced part of the power has to go through the wired connection to the device, allowing a more efficient use of the energy, and also lower requirements for this cable.

Reducing the weight (and increased wearing comfort) of the head-mounted device is all the more important as the current application focuses on keeping the head still during the operation, wherein the holding still below a certain threshold of motion triggers the calibration of the operational parameters. Many actions where remote assistance/monitoring is relevant often take a long time, such as medical procedures. Certainly in such a case, it is crucial that a user can also act consciously during that long length of time, and that they can control the calibration in a targeted manner.

In a preferred embodiment, the device further comprises an external control unit, the external control unit being wiredly or wirelessly, preferably wiredly, in communication with the head-mounted device, and preferably comprising a processor unit for controlling the head-mounted device; wherein the external control unit comprises a power source for supplying power to the head-mounted device and wherein the head-mounted device does not comprise a power source.

In a preferred embodiment, the parameters are stored on a memory element, preferably forming part of an external control unit, the external control unit being wiredly or wirelessly in communication with the head-mounted device and configured to control the head-mounted device, and wherein the external control unit further comprises a processor unit configured to request the stored parameters and to apply the stored parameters to the image sensor.

Preferably, the memory element is on an external control unit in line with outsourcing as many data processing tasks and others as possible to the external unit, as well as reducing the weight in the head-mounted device. Particularly in combination with a processor unit in the external control unit, it is of great advantage to also provide memory elements there.

In variations thereon, at least one and preferably all memory elements are located on the head-mounted device, more preferably together with at least one processor unit in communication with the memory elements.

In a second aspect, the invention relates to the use of the head-mounted device according to one or more of the embodiments according to the first aspect, by a medical professional (doctor, anesthetist, nurse, etc.) during a surgical procedure. Further applications are, for example, in interventions on location (for example with an ambulance, but also police, technical interventions, fire brigade, etc.). The benefits of a simplified auto-calibration of a head-mounted device in this application are clear and have already been discussed, including preserving sterility, as well as avoiding an impact on wearer concentration.

In a third aspect, the invention relates to a method of imaging with a head-mounted device according to the first aspect of the invention, wherein the parameters under which the image sensor of the head-mounted device operates, are automatically calibrated, when the head-mounted device during at least a predetermined period of time, wherein the predetermined length of time is preferably at least 1.0 s, and more preferably at least 2.0 s, detects that the translation of the head-mounted device is below a predetermined translational threshold and the rotation of the head-mounted device is below a predetermined rotational threshold, wherein the predetermined translational threshold is preferably at most 5.0 cm, more preferably at most 2.0 cm, and wherein the predetermined rotational threshold is preferably at most 10.0°, more preferably at most 5.0°, wherein the automatic calibration is performed based on the scene recorded by the image sensor; even more preferably wherein the predetermined translational threshold is at most 1.0 cm, and wherein the predetermined rotational threshold is at most 5.0°, and more preferably at most 0.5 cm and 2.5°; or even 0.25 cm and 1.0°; or even 0.1 cm and 0.5°.

The associated advantages are similar to those described for the device of the invention.

In what follows, the invention is described by way of non-limiting examples illustrating the invention, and which are not intended to and should not be interpreted as limiting the scope of the invention.

FIG. 1 shows a possible embodiment of the invention, in the form of smartglasses (1), comprising a holder with a display (2), and wherein a camera or image sensor (3) is provided on the bridge between the two glasses (5). A number of electronic components (4) are incorporated in the glasses at various places, such as on the holder, but also in the arms of the glasses.

Figure 2:
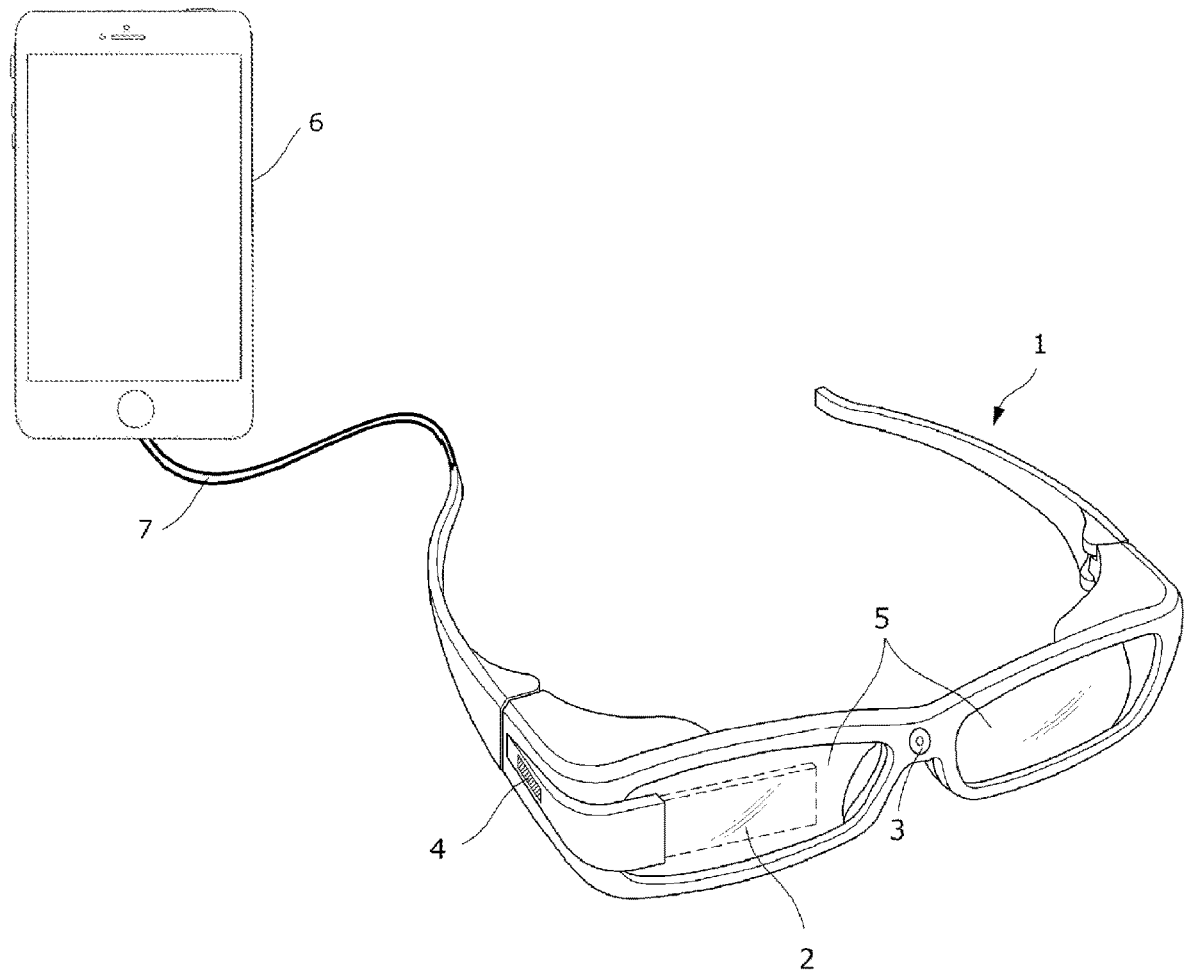
FIG. 2 shows an embodiment of a head-mounted device according to the invention in the form of smartglasses with a display, and an external control unit wiredly connected to the smartglasses.

FIG. 2 shows a possible variation on this, wherein a number of electronic components are provided in an external control unit (6), in this case a smartphone, which is wiredly (7) connected to the smartglasses (1). A number of the electronic components are no longer provided in the smartglasses, but their functionality is supported by the external control unit. This typically comprises power supply (battery), processor, etc.

Figure 3:
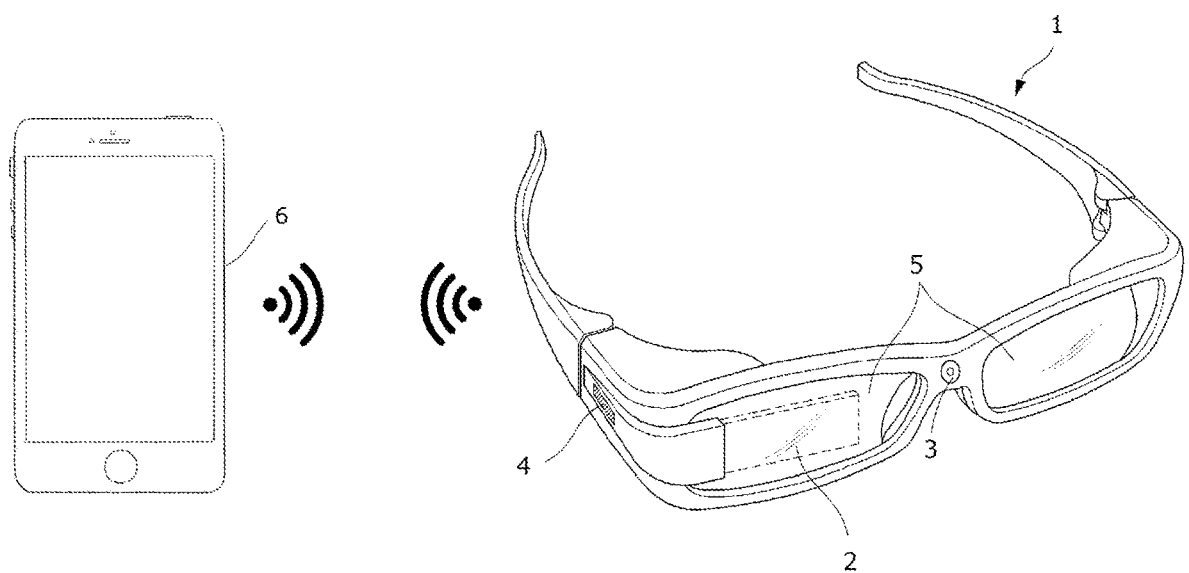
FIG. 3 shows an embodiment of a head-mounted device according to the invention in the form of smartglasses with a display, with all components provided on the head-mounted device, and an external control unit wirelessly connected to the smartglasses.

FIG. 3 shows an adaptation of the version from FIG. 2, wherein the communication between smartglasses and external control unit is wireless, by providing wireless communication components in the smartglasses and in the external control unit.

The present invention should not be construed as being limited to the embodiments described above and certain modifications or changes may be added to the examples described without having to re-evaluate the appended claims. For example, the present invention has been described with reference to medical procedures, but it should be understood that the invention can be applied to e.g. bomb dismantling or maintenance, or repair works in areas difficult to access (aerial work platform, space station, Arctic facility, etc.).

The invention claimed is:

1. A head-mounted device comprising:
   at least one sensor system for detecting translation and rotation of the head-mounted device; and
   an image sensor for recording images;
   the head-mounted device being configured to automatically calibrate parameters under which the image sensor operates when a detected translation remains below a predetermined translational threshold and a detected rotation remains below a predetermined rotational threshold for at least a predetermined period of time;
   wherein the predetermined length of time is at least 1.0 s, wherein the predetermined translational threshold is at most 5.0 cm, wherein the predetermined rotational threshold is at most 10.0°, and wherein the automatic calibration is performed based on the scene recorded by the image sensor;
   wherein the head-mounted device is configured not to perform the subsequent calibration until translation and/or rotation of the head-mounted device is detected by the sensor system that exceeds at least a predetermined movement threshold, the predetermined movement threshold being at least two times higher than the predetermined translational threshold and rotational threshold.

2. The head-mounted device according to claim 1, wherein the predetermined length of time is at least 2.0 s.

3. The head-mounted device according to claim 1, wherein the predetermined translational threshold is at most 3.0 cm.

4. The head-mounted device according to claim 1, wherein the predetermined rotational threshold is at most 5.0°.

5. The head-mounted device according to claim 1, wherein the calibration includes automatically finding shutter speed and setting focal length.

6. The head-mounted device according to claim 1, wherein the head-mounted device is a pair of smartglasses.

7. The head-mounted device according to claim 1, wherein the predetermined length of time is at least 2.0 s; wherein the predetermined translational threshold is at most 3.0 cm; and wherein the predetermined rotational threshold is at most 5.0°.

8. The head-mounted device according to claim 1, wherein the device is configured to perform the calibration if the detected translation is below the predetermined translational threshold and the detected rotation is below the predetermined rotational threshold for at least the predetermined length of time following the detection of a predetermined movement sequence of the head-mounted device, the detection being performed by the sensor system of the head-mounted device.

9. The head-mounted device according to claim 1, wherein the sensor system comprises at least one gyroscope.

10. The head-mounted device according to claim 1, wherein the sensor system comprises at least one accelerometer.

11. The head-mounted device according to claim 1, further comprising a display for displaying images, wherein a processor unit controls the display, and the display is configured to be positioned to display the images visible to a user wearing the head-mounted device on their head, wherein the processor unit is included in an external control unit, wiredly or wirelessly in communication with the head-mounted device and configured to control the head-mounted device.

12. The head-mounted device according to claim 11, wherein the display is configured to display images recorded by the image sensor.

13. The head-mounted device according to claim 1, further comprising an external control unit, the external control unit wiredly or wirelessly in communication with the head-mounted device; wherein the external control unit comprises a power source for supplying power to the head-mounted device and wherein the head-mounted device does not comprise a power source.

14. The head-mounted device according to claim 1, wherein the parameters are stored on a memory element forming part of an external control unit, the external control unit being wiredly or wirelessly in communication with the head-mounted device and configured to control the head-mounted device, and wherein the external control unit further comprises a processor unit configured to request the stored parameters and to apply the stored parameters to the image sensor.

15. The head-mounted device according to claim 14, wherein the memory element is part of the external control unit.

16. The head-mounted device according to claim 1, wherein the sensor system comprises one or more magnetometers.

17. Use of the head-mounted device according to claim 1 by a medical professional in a surgical procedure.

18. A method for imaging with the head-mounted device according to claim 1 comprising,
- recording a scene by the image sensor on the head-mounted device;
- automatically calibrating the parameters under which the image sensor of the head-mounted device operates, wherein the parameters are automatically calibrated when the head-mounted device detects for at least the predetermined length of time that the translation of the head-mounted device is below the predetermined translational threshold and the rotation of the head-mounted device is below the predetermined rotational threshold, and wherein the automatic calibration is performed based on the scene recorded by the image sensor.

* * * * *